(12) United States Patent
Chu et al.

(10) Patent No.: US 8,628,785 B2
(45) Date of Patent: Jan. 14, 2014

(54) METHOD FOR AUGMENTING THE IMMUNOGENICITY OF AN ANTIGEN

(75) Inventors: Ching-Liang Chu, Miaoli County (TW); Tzu-Chih Chen, Taipei (TW)

(73) Assignee: Yeastern Biotech Co., Ltd, Taipei (TW)

( * ) Notice: Subject to any disclaimer, the term of this patent is extended or adjusted under 35 U.S.C. 154(b) by 142 days.

(21) Appl. No.: 13/163,018

(22) Filed: Jun. 17, 2011

(65) Prior Publication Data

US 2011/0280906 A1    Nov. 17, 2011

Related U.S. Application Data

(63) Continuation-in-part of application No. 12/467,126, filed on May 15, 2009.

(60) Provisional application No. 61/054,081, filed on May 16, 2008.

(51) Int. Cl.
*A61K 39/00*    (2006.01)
*A61K 45/00*    (2006.01)
*A61K 47/00*    (2006.01)
*A61K 48/00*    (2006.01)

(52) U.S. Cl.
USPC .................. 424/274.1; 424/278.1; 514/44 R

(58) Field of Classification Search
None
See application file for complete search history.

(56) References Cited

U.S. PATENT DOCUMENTS

2009/0042776 A1*    2/2009    Ko et al. .................. 514/12

FOREIGN PATENT DOCUMENTS

| CN | 1939532 A | | 4/2007 | |
|---|---|---|---|---|
| TW | 200726775 A | | 7/2007 | |
| WO | WO 2005/040375 | * | 5/2005 | ............. C12N 15/10 |

OTHER PUBLICATIONS

Kino et al., 'An immunomodulating protein, Ling-Zhi-8 (LZ-8) prevents insulitis in non-obese diabetic mice.' Diabetologia, vol. 33:713-718, 1990.*
Lin et al. 'A Novel Adjuvant Ling Zhi-8 Enhances the Efficacy of DNA Cancer Vaccine by Activating Dendritic Cells.' Molecular Therapy 19(suppl. 1):S197, Abstract 512, 2011.*
Lin et al. 'A Novel Adjuvant Ling Zhi-8 Enhances the Efficacy of DNA Cancer Vaccine by Activating Dendritic Cell.' Human Gene Therapy 21(10):1443, Abstract P130, 2010.*
Lin et al. 'Delivery of noncarrier naked DNA vaccine into the skin by supersonic flow induces a polarized T helper type 1 immune response to cancer.' J. Gene Med. 10:679-689, 2008.*
Kino et al. 'Isolation and Characterization of a New Immunomodulatory Protein, Ling Zhi-8 (LZ-8), from *Ganoderma lucidium*.' J. Biol. Chem. 264:472-478, 1989.*

* cited by examiner

*Primary Examiner* — Nora Rooney
(74) *Attorney, Agent, or Firm* — WPAT, P.C.; Anthony King

(57) ABSTRACT

The present invention relates to a method for augmenting the immunogenicity of an antigen in a mammal, comprising immunizing the mammal with a composition comprising the antigen, and an adjuvant in an amount of effective to augment the immunogenicity of said antigen, wherein the adjuvant comprises a Ling-Zhi-8 (LZ-8) protein.

7 Claims, 8 Drawing Sheets

METHOD FOR AUGMENTING THE IMMUNOGENICITY OF AN ANTIGEN

CROSS-REFERENCE TO RELATED APPLICATIONS

This application is a Continuation-in-part of the pending U.S. patent application Ser. No. 12/467,126 filed on May 15, 2009, which claims priority to U.S. Application No. 61/054,081, filed on May 16, 2008, that is incorporated herein by reference in its entirety. Part of the data of this application used was published online on Apr. 17, 2011, by journal "Cancer Immunol Immunother".

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention relates to a method for augmenting the immunogenicity of an antigen. More particularly, the present invention relates to the use of a protein as adjuvant to augment the immunogenicity of antigens from pathogens and tumors.

DESCRIPTION OF PRIOR ART

The successful elimination of pathogens, neoplastic cells, or self-reactive immune mechanisms following prophylactic or therapeutic immunization depends to a large extent on the ability of the host's immune system to become activated in response to the immunization and mount an effective response, preferably with minimal injury to healthy tissue.

The rational design of vaccines initially involves identification of immunological correlates of protection—the immune effector mechanism(s) responsible for protection against disease—and the subsequent selection of an antigen that is able to elicit the desired adaptive response. Once this appropriate antigen has been identified, it is essential to deliver it effectively to the host's immune system.

In the design of effective vaccines, immunological adjuvants serve as critical components, which accelerate, prolong, and/or enhance an antigen-specific immune response as well as provide the selective induction of the appropriate type of response.

The immunogenicity of a relatively weak antigen can be enhanced by the simultaneous or more generally conjoined administration of the antigen with an "adjuvant", usually a substance that is not immunogenic when administered alone, but will evoke, increase and/or prolong an immune response to an antigen. In the absence of adjuvant, reduced or no immune response may occur, or worse the host may become tolerized to the antigen.

Adjuvants can be found in a group of structurally heterogeneous compounds. Classically recognized examples of adjuvants include oil emulsions (e.g., Freund's adjuvant), saponins, aluminium or calcium salts (e.g., alum), non-ionic block polymer surfactants, lipopolysaccharides (LPS), mycobacteria, tetanus toxoid, and many others. Theoretically, each molecule or substance that is able to favor or amplify a particular situation in the cascade of immunological events, ultimately leading to a more pronounced immunological response can be defined as an adjuvant.

In principle, through the use of adjuvants in vaccine formulations, one can (1) direct and optimize immune responses that are appropriate or desirable for the vaccine; (2) enable mucosal delivery of vaccines, i.e., administration that results in contact of the vaccine with a mucosal surface such as buccal or gastric or lung epithelium and the associated lymphoid tissue; (3) promote cell-mediated immune responses; (4) enhance the immunogenicity of weaker immunogens, such as highly purified or recombinant antigens; (5) reduce the amount of antigen or the frequency of immunization required to provide protective immunity; and (6) improve the efficacy of vaccines in individuals with reduced or weakened immune responses, such as newborns, the aged, and immunocompromised vaccine recipients.

As different adjuvants may have diverse mechanisms of action, their being chosen for use with a particular vaccine may be based on the route of administration to be employed, the type of immune responses desired (e.g., antibody-mediated, cell-mediated, mucosal, etc.), and the particular inadequacy of the primary antigen.

Accordingly, there is a great need in the art to develop new adjuvants that would combine low toxicity and easy availability with the ability to enhance and/or prolong the antigen-specific immune responses to a significant degree. The present invention addresses these and other needs in the art by providing glycosylceramides, a novel group of adjuvants with superior properties. Such adjuvants can improve prophylactic and/or therapeutic vaccines for the treatment of various infections and cancers.

DNA vaccination is a powerful strategy for antigen-specific immunotherapy against various diseases, including cancer. They can be repeatedly administered, high temperature stability, easily prepared in large scale with high purity and ability to induce long-lasting immune responses. The preclinical studies reveal that DNA vaccines can generate antigen-specific immunity against established tumors; however, the low efficacy of DNA vaccines in large animals and human has impaired their practical use. Therefore, development of novel approaches to increase the DNA vaccine potency is a primary goal in cancer therapy. Identification of a strong adjuvant is one strategy for enhancing the immunogenicity of DNA vaccine.

Dendritic cells (DCs) are professional antigen-presenting cells and play a critical role in initiating immune responses induced by vaccine. Toll-like receptors (TLRs) play an important role in the innate recognition of pathogen-associated molecular patterns (PAMPs) and initiation of immune responses in DCs. Because of the key regulatory role in immune responses, DCs are being developed as potent new vaccines for the treatment of cancer and viral infections. In addition, finding materials that can modulate the DC function is an emerging field that is developing alongside DC immunobiology. Natural or artificial substances that promote DC activation can potentially be adjuvant candidates and applied to immunotherapy and vaccination.

A number of pharmaceutically active compounds have been isolated from *Ganoderma lucidum*, a well-known medicinal fungus in Asia (Boh B et al. (2007) Biotechnol Annu Rev 13: 265-301; Sanodiya B S et al. (2009) Curr Pharm Biotechnol 10: 717-742). A fungal immunomodulatory protein (FIP) Ling Zhi-8 (LZ-8) is isolated from *G. lucidum* mycelia (Kino K et al. (1989) J Biol Chem 264: 472-478), and forms a FIP family together with FIP-gts (identical to LZ-8 but isolated from *G. tsugae*), FIP-fve (from *Flammulina veltipes*), FIP-vvo (from *Volvariella volvacea*), and FIP-gsi (from *G. sinensis*) (Lin W H et al. (1997) J Biol Chem 272: 20044-20048; Hsu H C et al. (1997) Biochem J 323 (Pt 2): 557-565; Li Q et al. (2010) Appl Biochem Biotechnol 162: 1403-1413). Some studies have shown the immunomodulatory effect of LZ-8 on autoimmunity and transplantation (van der Hem L G. et al. (1996) Transplant Proc 28: 958-959), and LZ-8 can also work as a mitogen to activate T cells (Hsu H Y et al. (2008) J Cell Physiol 215:15-26). Recently, the immunostimulatory effect of LZ-8 on human DCs has been reported (Lin Y L et al. (2009) J Leukoc Biol 86: 877-889), implying that LZ-8 may be an adjuvant candidate. However, there is no evidence for applying LZ-8 in vaccination or cancer therapy yet.

SUMMARY OF THE INVENTION

Figure 1A:
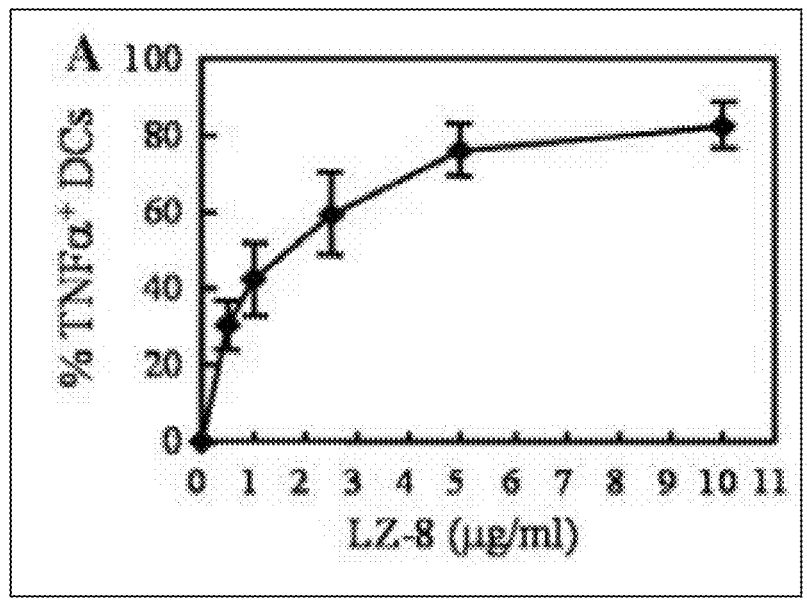
FIG. 1 shows that the stimulatory activity of LZ-8 on DCs is not due to contamination. Dotted line represents staining with an isotype-matched control antibody. All data are representative of two to four independent experiments.

The present invention relates to a method for augmenting the immunogenicity of an antigen in a mammal, comprising immunizing the mammal with a composition comprising the antigen, and an adjuvant in an amount of effective to augment the immunogenicity of said antigen, wherein the adjuvant comprises a Ling-Zhi-8 (LZ-8) protein.

DETAILED DESCRIPTION OF THE INVENTION

The terms "adjuvant" and "immunoadjuvant" are used interchangeably in the present invention and refer to a compound or mixture that may be non-immunogenic when administered to a host alone, but that augments the host's immune response to another antigen when administered conjointly with that antigen.

Adjuvant-mediated enhancement and/or extension of the duration of the immune response can be assessed by any method known in the art including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; and (iii) an increase in the level of one or more Type I cytokines The adjuvant of the invention can be administered as part of a pharmaceutical or vaccine composition comprising an antigen or as a separate formulation, which is administered conjointly with a second composition containing an antigen. In any of these compositions glycosylceramide can be combined with other adjuvants and/or excipients/carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues, polyphosphazenes, or synthetic polynucleotides, and surface active substances such as lysolecithin, pluronic polyols, polyanions, peptides, hydrocarbon emulsions, or keyhole limpet hemocyanins (KLH). Preferably, these additional adjuvants are also pharmaceutically acceptable for use in humans.

The term "immunogenic" means that an agent is capable of eliciting a humoral or cellular immune response, and preferably both. An immunogenic entity is also antigenic. An immunogenic composition is a composition that elicits a humoral or cellular immune response, or both, when administered to an animal having an immune system.

The term "antigen" refers to any agent (e.g., protein, peptide, polysaccharide, glycoprotein, glycolipid, nucleic acid, or combination thereof) that, when introduced into a host, animal or human, having an immune system (directly or upon expression as in, e.g., DNA vaccines), is recognized by the immune system of the host and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR). Within the meaning of the present invention, the antigens are preferably "surface antigens", i.e., expressed naturally on the surface of a pathogen, or the surface of an infected cell, or the surface of a tumor cell. A molecule that is antigenic need not be itself immunogenic, i.e., capable of eliciting an immune response without an adjuvant or carrier.

The term "vaccine" refers to a composition (e.g., protein or vector such as, e.g., an adenoviral vector, Sindbis virus vector, or pox virus vector) that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs, e.g., to prevent organ rejection or suppress an autoimmune condition). Vaccine efficacy can be established in animal models.

The term "DNA vaccine" is an informal term of art, and is used herein to refer to a vaccine delivered by means of a recombinant vector. An alternative, and more descriptive term used herein is "vector vaccine" (since some potential vectors, such as retroviruses and lentiviruses are RNA viruses, and since in some instances non-viral RNA instead of DNA is delivered to cells through the vector). Generally, the vector is administered in vivo, but ex vivo transduction of appropriate antigen presenting cells, such as dendritic cells (DC), with administration of the transduced cells in vivo, is also contemplated.

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease. Preferably, the disease is either infectious disease (e.g., viral, bacterial, parasitic, or fungal) or malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.).

Immune systems are classified into two general systems, the "innate" or "natural" immune system and the "acquired" or "adaptive" immune system. It is thought that the innate immune system initially keeps the infection under control, allowing time for the adaptive immune system to develop an appropriate response. Recent studies have suggested that the various components of the innate immune system trigger and augment the components of the adaptive immune system, including antigen-specific B and T lymphocytes.

The term "innate immunity" or "natural immunity" refers to innate immune responses that are not affected by prior contact with the antigen. Cells of the innate immune system, including macrophages and dendritic cells (DC), take up foreign antigens through pattern recognition receptors, combine peptide fragments of these antigens with MHC class I and class II molecules, and stimulate naive $CD8^+$ and $CD4^+$ T cells respectively. Professional antigen-presenting cells (APC) communicate with these T cells leading to the differentiation of naive $CD4^+$ T cells into T-helper 1 (Th1) or T-helper 2 (Th2) lymphocytes that mediate cellular and humoral immunity, respectively.

The term "acquired immunity" or "adaptive immunity" is used herein to mean active or passive, humoral or cellular immunity that is established during the life of an animal, is specific for the inducing antigen, and is marked by an enhanced response on repeated encounters with said antigen. A key feature of the T lymphocytes of the adaptive immune system is their ability to detect minute concentrations of pathogen-derived peptides presented by MHC molecules on the cell surface.

The term "augment the immune response" means enhancing or extending the duration of the immune response, or both. When referred to a property of an agent (e.g., adjuvant), the term "[able to] augment the immunogenicity" refers to the ability to enhance the immunogenicity of an antigen or the ability to extend the duration of the immune response to an antigen, or both.

The term "enhance immune response" within the meaning of the present invention refers to the property or process of increasing the scale and/or efficiency of immunoreactivity to a given antigen, said immunoreactivity being either humoral or cellular immunity, or both. An immune response is believed to be enhanced, if any measurable parameter of antigen-specific immunoreactivity (e.g., antibody titer, T cell production) is increased at least two-fold, preferably ten-fold, most preferably thirty-fold.

The term "therapeutically effective" applied to dose or amount refers to that quantity of a compound or pharmaceutical composition or vaccine that is sufficient to result in a desired activity upon administration to a mammal in need thereof. As used herein with respect to adjuvant—and antigen-containing compositions or vaccines, the term "therapeutically effective amount/dose" is used interchangeably with the term "immunogenically effective amount/dose" and refers to the amount/dose of a compound (e.g., an antigen and/or an adjuvant comprising glycosylceramide) or pharmaceutical composition or vaccine that is sufficient to produce an effective immune response upon administration to a mammal.

The term "pharmaceutically acceptable", as used in connection with compositions of the invention, refers to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

A "nucleic acid molecule" (or alternatively "nucleic acid") refers to the phosphate ester polymeric form of ribonucleosides (adenosine, guanosine, uridine, or cytidine: "RNA molecules") or deoxyribonucleosides (deoxyadenosine, deoxyguanosine, deoxythymidine, or deoxycytidine: "DNA molecules"), or any phosphoester analogs thereof, such as phosphorothioates and thioesters, in either single stranded form, or a double-stranded helix. Oligonucleotides (having fewer than 100 nucleotide constituent units) or polynucleotides are included within the defined term as well as double stranded DNA-DNA, DNA-RNA, and RNA-RNA helices. This term, for instance, includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

The present invention relates to a method for augmenting the immunogenicity of an antigen in a mammal, comprising immunizing the mammal with a composition comprising (i) the antigen, and (ii) an adjuvant in an amount of effective to augment the immunogenicity of said antigen, wherein the adjuvant comprises a Ling-Zhi-8 (LZ-8) protein.

Preferably, the antigen of the invention is a protein or a naked DNA, more preferably, the antigen of the invention is a naked DNA, most preferably, the antigen of the invention is a HER-2/neu DNA, which is delivered by gene gun. The protein of the present invention is an inactivated virus, a cancer cell extract or a recombinant protein Preferably, the LZ-8 protein of the present invention is isolated from *Ganoderma lucidum* or prepared by recombinant protein technology in yeast or bacterium system. Preferably, the antigen and the adjuvant of the present invention are administered simultaneously. Preferably, the method for augmenting the immunogenicity of the present invention is manifested by the enhancement of the T helper 1 (Th1) and cytotoxic T lymphocyte (CTL) response.

The present invention investigates whether LZ-8 can improve the immunogenicity of DNA vaccine in a preclinical model used HER-2/neu as antigen (Lin C C et al. (2004) Mol Ther 10: 290-301). The results shows that recombinant LZ-8 activated mouse DCs as it did in human DCs via TLR4. Significantly, LZ-8 co-treatment enhances the therapeutic efficacy of HER-2/neu DNA vaccine against HER-2/neu-overexpressing tumor and this promoting effect is mediated by TLR4 in vivo. Thus, the present invention demonstrates that LZ-8 could be a novel adjuvant and has potential to apply in cancer therapy and vaccination.

One embodiment of the present invention demonstrates that LZ-8 exhibits potent activating activities on mouse DCs and enhances the efficacy of DNA vaccine against cancer. Interestingly, the immunostimulatory function of LZ-8 is dependent on TLR4 in vivo. Thus, the present invention provides convincing evidences that LZ-8 is a novel adjuvant for DNA vaccine in cancer therapy.

DNA vaccine has been well-established in animal models for preventing and treating various diseases; however, low immunogenicity is the major obstacle for the development of DNA vaccines in large animal models and human. The present invention has tried several approaches to overcome this hurdle, including fusion to activating cytokine genes, alternation of administration route, treatment of Geldanamycin/indoleamine 2,3-dioxygenase siRNA/histone deacetylase inhibitor/a fungal extract, delivery by gene gun, and DNA formulation. The present invention reports an effective immunostimulator LZ-8 to strengthen the immunogenicity. Similar strategy has been shown by using heat shock proteins (HSPs). It will be valuable to compare the effect of LZ-8- to HSP-DNA vaccine on cancer therapy.

Very interestingly, LZ-8 (FIG. 1B), as well as HSP70, enhance the immune responses via TLR4. Although TLR4 is well-known for its role in sensing LPS, various proteins from pathogens and host-derived damage-associated molecular patterns (DAMPs) have pro-inflammatory activity via TLR4 pathway. However, the stimulatory activity of HSP70 has been argued by microbial contaminants introduced during the purification of proteins. The present invention has used various approaches, as proposed previously, to vigorously rule out the possible microbial contamination in the LZ-8 preparation (FIGS. 1C-F). The activity of LZ-8 was not completely removed by boiling (FIG. 1F), probably because of the heat-resistant property of LZ-8. Therefore, the present invention concludes that the immunostimulatory activity is specifically attributed to LZ-8.

Figure 4A:
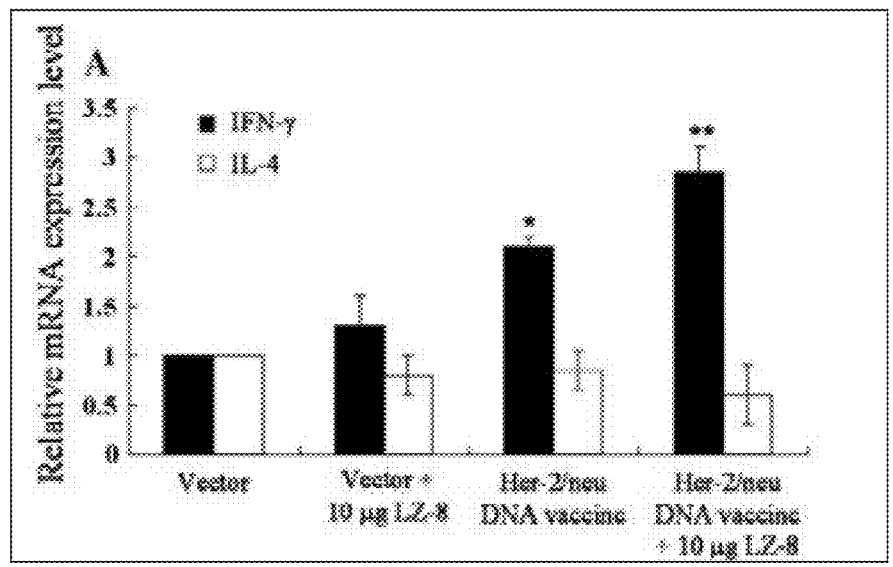
FIG. 4 shows that LZ-8 promotes Th1 differentiation and CTL response to MBT-2 cells in vaccinated mice. The data are presented as the mean±SD of three mice. The symbol (**) indicates a statistically significant difference when compared LZ-8-treated to untreated DNA vaccinated mice ($p<0.05$). The symbol (*) indicates a statistically significant difference when compared DNA vaccine-treated to control vector-treated mice ($p<0.001$). All data are representative of two to three independent experiments.

An ideal adjuvant for the cancer vaccine should strongly elicit cellular responses, especially anti-cancer CTL activity. The present invention has shown that LZ-8 uniquely promotes Th1 differentiation (FIGS. 2 and 4). Thus, LZ-8 could be more suitable than some clinical adjuvants, such as alum which mainly induces humoral responses, in cancer vaccine development. For developing LZ-8 into a new adjuvant, one practical consideration is to ensure a stable supply of LZ-8 with good quality. Some expression systems have been reported to obtain high amount of LZ-8; however, LZ-8 prepared from these systems have various levels of activity. The present invention has generated large scale of LZ-8 with stable activity from *S. cerevisiae* system. For example, although the activating effect of LZ-8 prepared from *Pichia pastoris* system on human DCs has been reported recently, the saturated dose of their LZ-8 for inducing cytokine production is at 50 µg/mL, which is much higher than the LZ-8 (5 µg/mL) (FIG. 1A) of the present invention. In addition, the LZ-8 of the present invention promoted IL-2 production by mouse DCs, which were not reported previously, and then may potentially facilitate NK cell activation to help killing cancer cells. Overall, the present invention has shown many results to confirm the availability of LZ-8 in vaccinology, especially the preclinical data from mouse model in vivo. It is feasible to further study the effect of LZ-8 on human and then hasten the clinical trial for LZ-8.

In summary, the present invention provides the first evidence to apply LZ-8 to a DNA vaccine model for cancer therapy and determine the immunogenicity in vivo. Because DCs have been used as a therapeutic vaccine, LZ-8 may also be used to enhance the efficiency of DC-based vaccine in cancer therapy. Furthermore, the LZ-8-HER2/neu DNA vaccine of the present invention also has application in breast cancer therapy and may be formulated in nanocarriers. Thus, the present invention provides a new insight for the application of LZ-8 not only in health food for enhancing immunity but also in vaccine technology for preventing and treating various cancer and infectious diseases.

EXAMPLES

The examples below are non-limiting and are merely representative of various aspects and features of the present invention.

Example 1

Materials and Methods

Mice and Cell Cultures

C57BL/6, C3H/HeN, and C3H/HeJ (TLR4 mutant) mice were purchased from National Laboratory Animal Center (Taipei, Taiwan) or National Cheng-Kung University (Tainan, Taiwan). OT-I and OT-II TCR transgenic mice were provided by Dr. Clifford Lowell (UCSF, San Francisco, Calif.). All mice were housed in the barrier facility at NHRI (Taiwan) under an Institutional Animal Care and Use Committee-approved protocol. Mouse DCs were generated from bone marrow as previously described. The murine bladder tumor cell line MBT-2 has been described and is known to express high levels of $p185^{neu}$.

Preparation and Inactivation of LZ-8

LZ-8 was cloned and expressed in *Saccharomyces cerevisiae*. Cells expressing LZ-8 (or empty vector as control) were disrupted, centrifuged, and the supernatant was passed through filter and molecular sieves to obtain proteins between 10 kDa and 100 kDa. The filtrate was further purified using FPLC with Superdex 75 columns (GE Healthcare). The purity was determined by FPLC. To inhibit LPS activity, the sample was treated with polymyxin B (5 µg/mL, Sigma-Aldrich) at 37° C. for 30 min. To inactivate LZ-8, the protein was treated with proteinase K (2 mg/mL, Promega) at 37° C. for 1 h or boiled at 100° C. for 50 min.

Detection of TNF-α Production

DCs were treated with LZ-8 for 6 h and the intracellular TNF-α was detected by anti-TNF-α mAb (Biolegend) as described previously. For quantifying the production of TNF-α, supernatants were collected from $1 \times 10^6$ DCs/ml after incubation with LZ-8 (5 µg/mL), LPS (20 ng/ml, Sigma-Aldrich), or CpG (500 nM, InvivoGen) for 6 h, and then assayed using ELISA kits (eBioscience).

Assays for T Cell Activation

Antigen presentation by DCs was determined as described previously. DCs were incubated with 1 µg/mL $OVA_{257-264}$ (OVA$_{P1}$) or OVA$_{323-339}$ (OVA$_{P2}$) (synthesized by Echo Chemical Co., Taiwan) in the presence or absence of LZ-8 for 3 h, and LZ-8 was washed out to avoid its mitogenic effect on T cells, and then OT-I or OT-II T cells were added to the culture. T cell proliferation was determined by [$^3$H] thymidine incorporation after 72 h. For recall assay in vivo, a subunit vaccine model was used. C57BL/6 mice were immunized with OVA$_{p2}$ (10 µg) mixed with incomplete Freund's Adjuvant (IFA, Sigma-Aldrich) alone or IFA and LZ-8 (10 µg) via footpad injection. Draining lymph node (LN) cells were isolated after 10 days and cultured with OVA$_{p2}$ for 3 days, and T cell proliferation was determined by [$^3$H] thymidine incorporation. Supernatants from DC-OT-I/OT-II or LN cell cultures were collected after 4 days and IFN-γ production was measured by ELISA (eBioscience).

Therapeutic Efficacy in a Mouse Model of Established MBT-2 Tumors

The MBT-2 tumor model was described previously. Briefly, MBT-2 cells (1×10$^6$) were injected subcutaneously (s.c.) into the flank of C3H/HeN (WT) or C3H/HeJ (TLR4 mutant) mice. Ten days after injection, the mice were immunized with the naked HER-2/neu DNA vaccine or pRc/CMV vector (10 µg) from the shaved abdominal region for three times at weekly intervals using a low pressure-accelerated gene gun (Bioware, Technologies Co. Ltd, Taipei, Taiwan), with or without LZ-8 treated by local intraperitoneal injection. The effects of these treatments on the growth of MBT-2 tumors were then monitored triple a week. Tumor size was calculated using the formula for a rational ellipse: (m$_1$×m$_2$× m$_2$×0.5236), where m$_1$ represents the longer axis and m$_2$ the shorter axis. Mice were euthanized when tumor size reached >2500 mm$^3$ in mean diameter.

Quantitative RT-PCR

After the last DNA vaccination for three days, inguinal LN cells (2×10$^6$ cells/well) from immunized C3H/HeN mice were stimulated with recombinant HER-2/neu protein (10 µg/mL, R&D Systems) in 24-well plate with complete RPMI 1640 medium. After 20 h, CD4$^+$ or CD8$^+$ T cells were purified by negative selection (Dyanl CD4 and CD8 Negative Isolation Kit, Dynal AS, Oslo, Norway; purity >90%). Then, total RNA was extracted by using TRIzol reagent (Invitrogen, Carlsbad, Calif., USA). The cDNA was generated from denatured total RNA using oligo dT as the primer and MMLV-Reverse Transcriptase (Promega, Madison, Wis., USA) according to the manufacturer's instructions as described previously. The used primers were: IFN-γ F: 5'-ACTG-GCAAAAGGATGGTGAC-3' (SEQ ID NO: 1) and R: 5'-ACCTGTGGGTTGTTGACCTC-3' (SEQ ID NO: 2); hypoxanthine guanine phosphoribosyl transferase 1 (HPRT), F: 5'-GTTGGATAAGGCCAGACTTTGTTG-3' (SEQ ID NO: 3) and R: 5'-GATTCAACTTGCGCCATCTTAGGC-3 (SEQ ID NO: 4). ABI 7500 Fast Real-Time system with SYBR Green PCR Master Mix (Applied Biosystems) was used for quantitative real-time PCR. The expression was normalized against to HPRT. These normalized data were then expressed relative to the vector control group.

Inguinal LN Cell-Mediated Cytotoxicity Assay for Targeting MBT-2 Cells

The protocol was modified from the previous report. In brief, inguinal LN cells from C3/HeN or C3/HeJ mice were cultured in complete RPMI 1640 medium and stimulated with recombinant HER-2/neu protein (10 µg) for 5 days. The antigen-stimulated cells (effector cells) were cocultured with 1×10$^4$ MBT-2-luciferase cells at various E:T ratios in 96-well round-bottomed plates for 12 h. Cytolysis was determined by quantitatively measuring luciferase activity in the supernatant from each well as reported previously.

Statistical Analysis

Statistical analysis in cytokine production, T-cell proliferation, depiction of tumor size, and CTL activity assay were evaluated by a Student's t-test with 2 sample equal variance with a 2 tailed distribution. Data are showed as mean±SD of three samples. The p<0.05 is considered statistically significant. For the comparison between the survival rates of various vaccinated mice, we used the Kaplan-Meier method and log-rank analysis using GraphPad Prism software package version 4.0 (GraphPad Software; San Diego, Calif., USA).

Example 2

The Activation of Mouse DCs by Recombinant LZ-8 was Not Due to Microbial Contaminants The stimulatory activity of LZ-8 on human DCs has been identified; however, the application of LZ-8 in vaccination and cancer therapy is not studied. Since the present invention used a mouse model to evaluate the adjuvant effect of LZ-8, the present invention first tested whether LZ-8 could activate mouse DCs. As shown in human DCs previously, LZ-8 promoted cytokine and chemokine production and maturation of bone marrow-derived DCs from C57BL/6 mice (FIG. 1A). The saturated dose of the LZ-8 for maximal TNF-α production was at 5 µg/mL. No significant cytotoxicity was observed at the highest dose of LZ-8 as measured by propidium iodide staining (data not shown). Furthermore, the LZ-8-induced TNF-α production was dramatically reduced in TLR4 mutant (C3H/HeJ) DCs when compared to WT (C3H/HeN) cells (FIG. 1B), consistent to the report in human DCs. A very important issue is that the present invention must rule out the effect of microbial contamination because the present invention used a yeast expression system to generate recombinant LZ-8 protein. Therefore, the present invention conducted a series of experiments to address this issue. First, the present invention prepared a control solution from yeasts that did not express LZ-8 but were processed in identical way to those expressing LZ-8, especially used the same column. FPLC analysis showed nothing in control solution except for a few of LZ-8, probably from the LZ-8 residues in column (FIG. 1C upper). This control solution did not activate DCs from C57BL/6 mice (FIG. 1C lower), indicating that the process of LZ-8 preparation did not introduce any microbial contaminant. Next, polymyxin B treatment did not significantly inhibit the activity of LZ-8, suggesting that endotoxin contamination was negligible (FIG. 1D). Furthermore, protein-ase K-digested (FIG. 1E) and heat-inactivated (FIG. 1F) LZ-8 lost the ability to stimulate DCs, illustrating that DCs were specifically activated by the LZ-8 protein. Overall, these data strongly argue against the possibility that any microbial contaminant would contribute to the activating effect of LZ-8 on DCs.

FIG. 1 shows that the stimulatory activity of LZ-8 on DCs was not due to contamination. Mouse bone marrow-derived DCs were incubated with LZ-8 at indicated doses. After 6 h, the percentages of TNF-α-producing CD11c$^+$ cells were determined by intracellular staining and flow cytometry. (A) Dose response curve of LZ-8 to DCs derived from C57BL/6 mice. (B) DCs derived from C3H/HeN (WT) and C3H/HeJ (TLR4 mutant) mice were untreated or treated with LZ-8 (5 µg/ml), LPS (20 ng/ml), or CpG (500 µM). Supernatants were collected after 6 h and TNF-α production was measured by ELISA. Error bars indicate ±SD of three samples. $^{NS}$p>0.05; **p<0.01 (Student's t-test) was comparison between WT and mutant cells. (C) Upper panels: The FPLC map for control solution (prepared from yeasts expressing empty vector) and LZ-8; Lower panels: DCs from C57BL/6 mice were untreated (gray line) or treated with LPS (20 ng/ml), LZ-8 (5 μg/ml), or control solution (black line) for 6 h, and the percentages of TNF-α-producing CD11c$^+$ cells were showed above the regional marker. (D-F) DCs were treated as in (C) except that LPS and LZ-8 were treated with polymyxin B (PMB) for 30 min (D), incubated with proteinase K (PK) for 1 h (E), or boiled for 25 and 50 min (F) before being added to DC cultures.

Example 3

LZ-8 Facilitated DC-Induced Ag-Specific T Cell Activation In Vitro and In Vivo

Figure 2A:
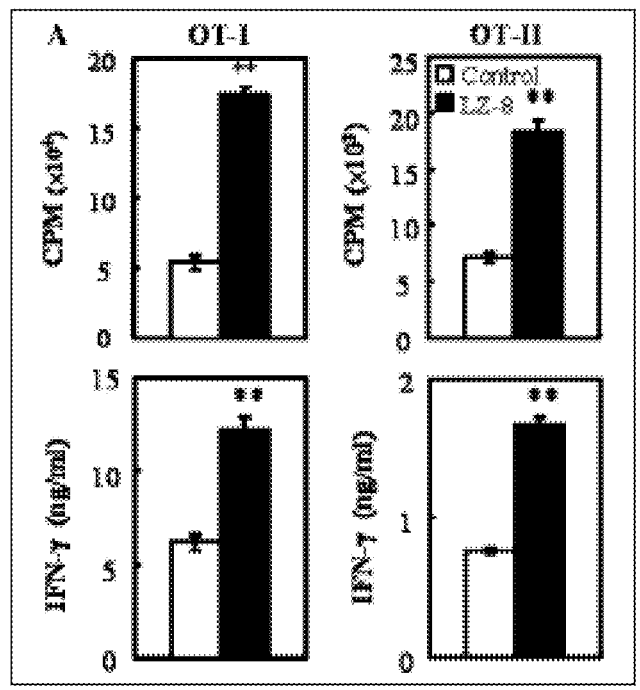
FIG. 2 shows that LZ-8 enhances the ability of DCs to induce Ag-specific T cell activation. Error bars indicate ±SD of three samples. *$p<0.05$; *$p<0.01$ (Student's t-test) is comparison between LZ-8-treated and untreated cells or mice. All data are representative of two to four independent experiments.
Figure 2B:
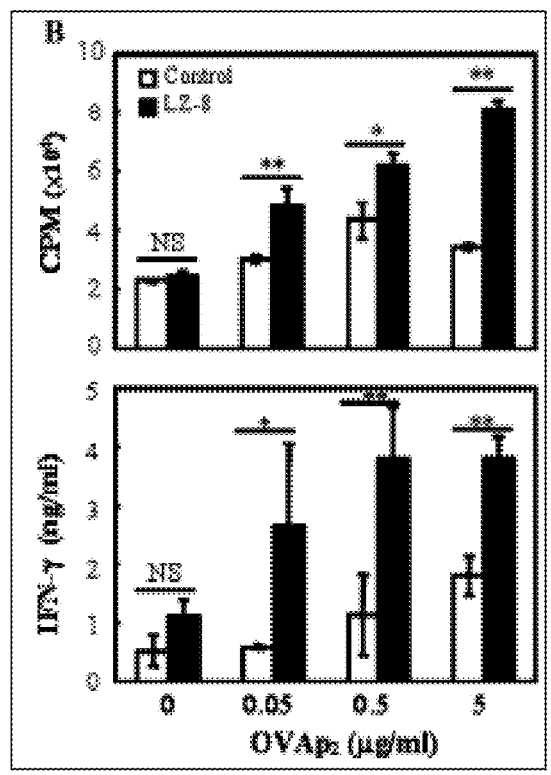

Induction of antigen-specific T cell activation is the primary function of mature DCs, the present invention next tested whether LZ-8-stimulated DCs are able to activate naïve T cells. OT-I or OT-II T cells were co-cultured with LZ-8-treated, $OVA_{P1}$- or $OVA_{P2}$-pulsed DCs, and T cell proliferation and IFN-γ production were determined. LZ-8-activated DCs induced more OVA-specific T cell proliferation and IFN-γ production than control cells in vitro (FIG. 2A). Then, a subunit vaccine model was performed to evaluate the adjuvant effect of LZ-8 on T cell priming in vivo. C57BL/6 mice were immunized with $OVA_{P2}$ mixed with IFA alone or IFA plus LZ-8, and draining LN cells were collected after 10 days. The LN T cells isolated from LZ-8-immunized mice showed more proliferation and IFN-γ production than cells from control mice in response to OVAp$_2$ (FIG. 2B). These data reveal that LZ-8-stimulated DCs can induce Ag-specific T cell activation both in vitro and in vivo. The secretion of IL-12 from DCs and the production of IFN-γ from activated T cells indicate that LZ-8-stimulated DCs preferentially promote Th1 differentiation.

FIG. 2 shows that LZ-8 enhanced the ability of DCs to induce Ag-specific T cell activation. (A) Untreated (control) or LZ-8 (5 μg/mL)-treated, $OVA_{P1}$ or $OVA_{P2}$ (1 μg/mL)-pulsed DCs were co-cultured with OT-I or OT-II T cells for 72 h. T cell proliferation was determined by [$^3$H] thymidine incorporation (upper panels), and IFN-γ production was measured by ELISA (lower panels). (B) C57BL/6 mice were immunized with $OVA_{P2}$ (10 μg) mixed with IFA alone (control) or IFA+LZ-8 (10 μg). Draining LN cells were collected after 10 days and cultured with indicated concentration of $OVA_{P2}$ for 3 days. T cell proliferation was determined by [$^3$H] thymidine incorporation (upper) and IFN-γ production was measured by ELISA (lower).

Example 4

LZ-8 Enhanced the Antitumor Effect of HER-2/neu DNA Vaccine

Figure 3:
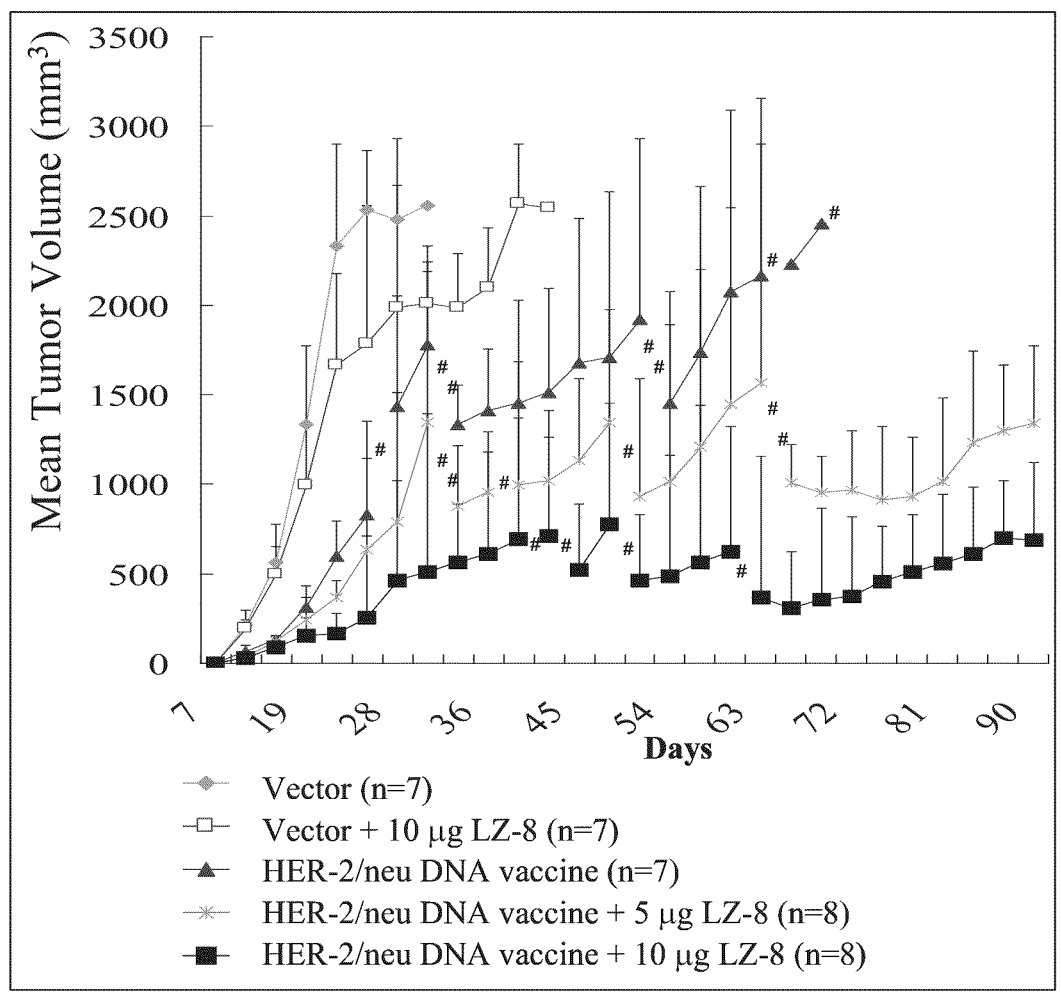
FIG. 3 shows that LZ-8 enhances the efficacy of HER-2/neu DNA vaccine against MBT-2 tumor in C3H/HeN mice. Error bars indicate +SD of remaining mice. Data are representative of three independent experiments.

Previous data demonstrated that gene gun-delivered naked HER-2/neu DNA vaccine has therapeutic effect on established p185$^{neu}$-expressing 40 expressing MBT-2 tumors in C3H/HeN mice (Lin C C et al. (2008) J Gene Med 10: 679-689). Based on this model, the present invention further tested whether LZ-8 can increase its efficacy. As shown in FIG. 3, immunization with neither the control vector alone nor LZ-8 alone could reduce tumor growth in mice, and all mice in these two groups had to be sacrificed due to the size of their tumors or their condition; it is expected that these mice would have become moribund by day 41 at the latest. In contrast, vaccination with the HER-2/neu DNA alone or HER-2/neu DNA plus LZ-8 (5 or 10 μg) significantly inhibited tumor growth after tumor implantation for 22 days. However, the HER-2/neu DNA plus LZ-8 was more effective than the HER-2/neu DNA alone in prolonging the survival of the mice. At day 63 after tumor cells implantation, all mice with HER-2/neu DNA vaccine alone had to be sacrificed, but 2/8 mice with HER-2/neu DNA vaccine plus 5 μg LZ-8 and 4/8 mice in HER-2/neu DNA vaccine plus 10 μg LZ-8 survived to day 90, at which time the experiment was terminated. These results clearly indicate that LZ-8 efficiently enhances the therapeutic efficacy of HER-2/neu DNA vaccine against p185$^{neu}$-expressing MBT-2 tumors in vivo.

FIG. 3 shows that LZ-8 enhanced the efficacy of HER-2/neu DNA vaccine against MBT-2 tumor in C3H/HeN mice. C3H/HeN mice were implanted with MBT-2 tumor cells and then vaccinated with various formulas as indicated. Line graphs showed the depiction of tumor volumes at the indicated time. The symbol (#) indicates that some mice were sacrificed due to the mean diameter of the tumor reaching 2500 mm$^3$ or the poor condition of the mice. Subsequently, the mean tumor volume was calculated from the remaining mice.

Example 5

LZ-8 Promoted the Th1 and CTL Responses Induced by HER-2/neu DNA Vaccination

Figure 4B:
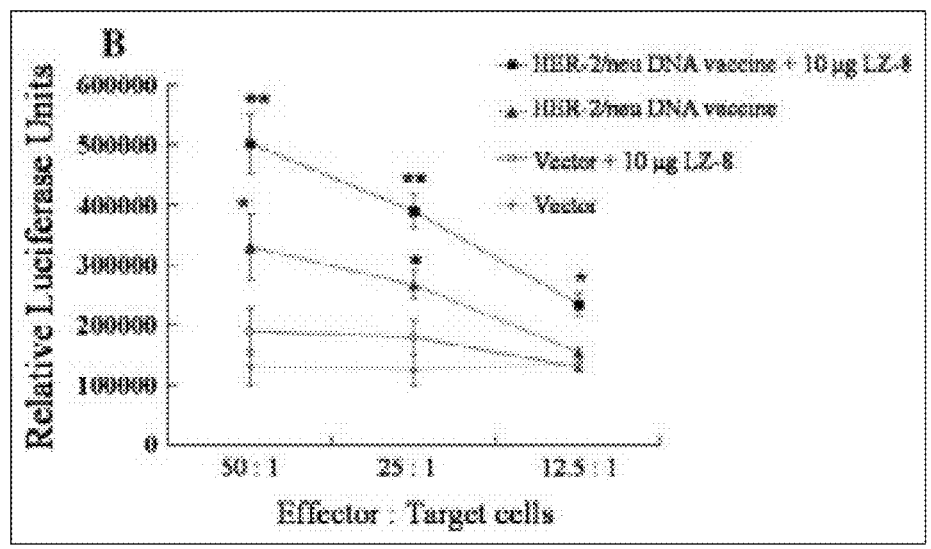

Th1-based immune responses have been identified to play a crucial role in suppressing implanted MBT-2 tumor in mice (Lai M D et al. (2010) Cancer Gene Ther 17:203-211; Lin C C et al. (2008) J Gene Med 10: 679-689). In addition, the present invention has showed that LZ-8-stimulated DCs preferentially facilitate Th1 differentiation (FIG. 2). Therefore, the present invention examined whether LZ-8 can promote Th1 responses induced by HER-2/neu DNA vaccination. LN cells collected from vaccinated mice were stimulated with recombinant HER-2/neu protein and the expression of IFN-γ (Th1) and IL-4 (Th2) was determined by quantitative real-time PCR. Mice immunized with HER-2/neu DNA vaccine plus LZ-8 produced significantly higher amount of IFN-γ than that immunized with HER-2/neu DNA vaccine alone (FIG. 4A), whereas no significant difference in IL-4 production. Since Th1 differentiation promotes cellular immune responses such as cytotoxic T lymphocyte (CTL) expansion and activation, the present invention further examined the CTLs responses in vaccinated mice. As shown in FIG. 4B, the LN cells collected from mice immunized with LZ-8 plus HER-2/neu DNA vaccine generated higher level of HER-2/neu-specific CTL response than that from the mice immunized with HER-2/neu DNA vaccine alone. The cells isolated form control vector-immunized mice showed no significant p185$^{neu}$-induced MBT-2 cytotoxicity. These data illustrate that LZ-8 promotes HER-2/neu-specific Th1 responses induced by HER-2/neu DNA vaccination, which could contribute to the enhancement of anti-tumor efficacy of HER-2/neu DNA vaccine.

FIG. 4 shows that LZ-8 promoted Th1 differentiation and CTL response to MBT-2 cells in vaccinated mice. The inguinal LN cells were isolated from vaccinated C3H/HeN mice as indicated formulas and then were stimulated with recombinant HER-2/neu protein (10 μg/mL). (A) After 3 days, the expression levels of IFN-γ or IL-4 mRNA expression in the stimulated CD4$^+$ T cells were determined using quantitative real time PCR. The data were normalized to HPRT expression in each sample and error bars indicate mean±SD of five mice. (B) After 5 days, the stimulated LN cells were collected as effector cells. CTL-mediated cytotoxicity assay was performed by incubating the stimulated LN cells with serial dilutions of MBT-2-luciferase cells (target cells), and then detecting luciferase activity in the supernatants.

Example 6

The Adjuvanticity of LZ-8 on HER-2/neu DNA Vaccine is Mediated Via TLR4

Figure 1B:
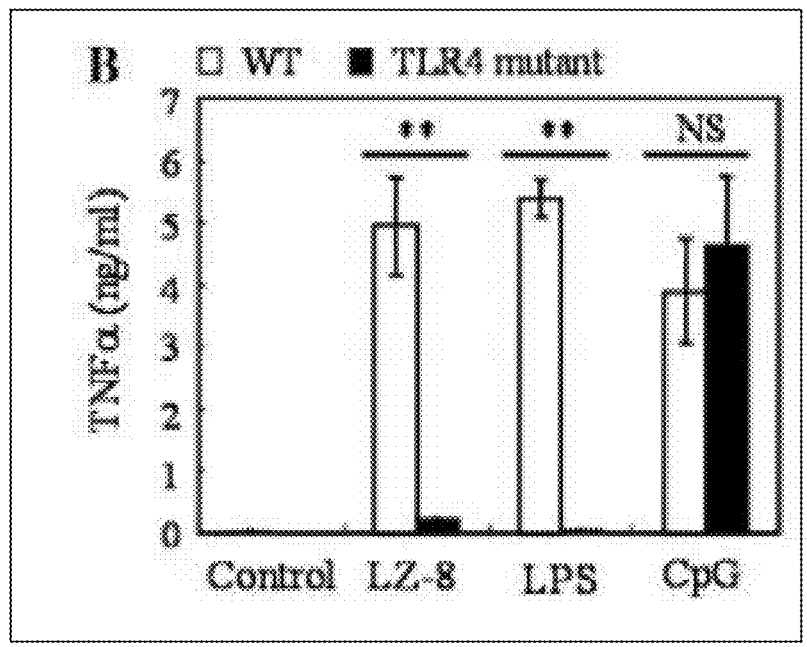
Figure 1C:
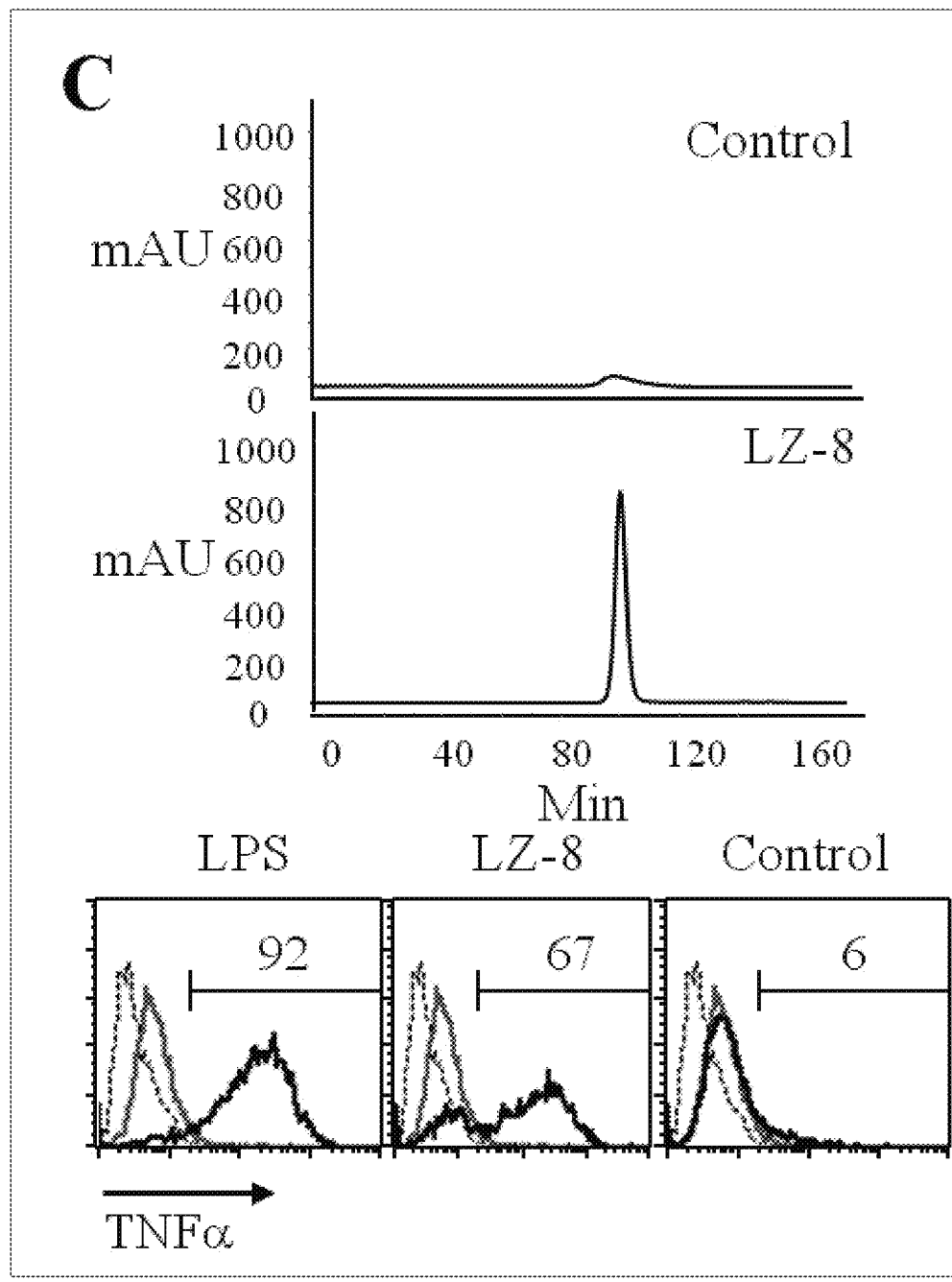
Figure 1D:
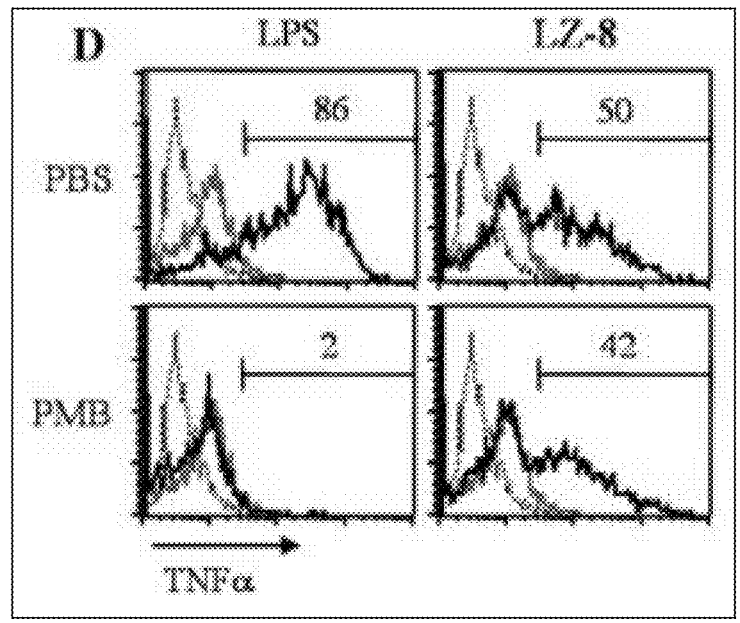
Figure 1E:
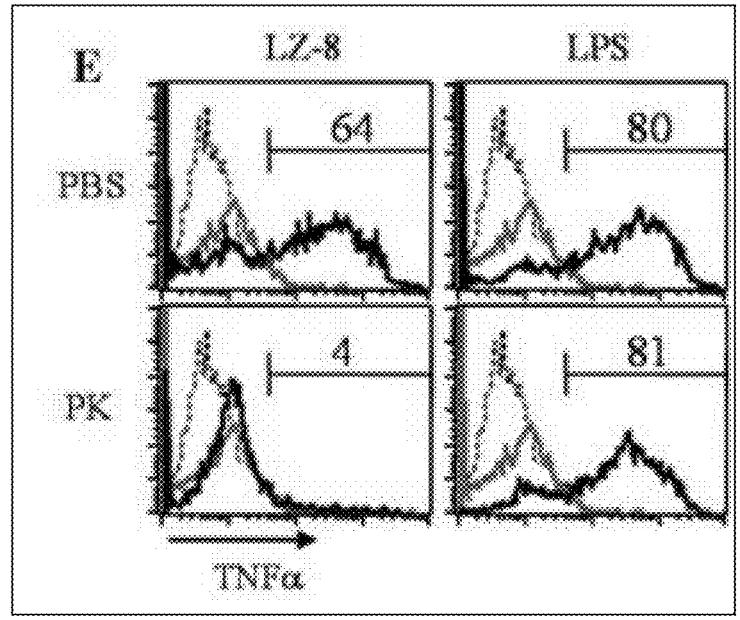
Figure 1F:
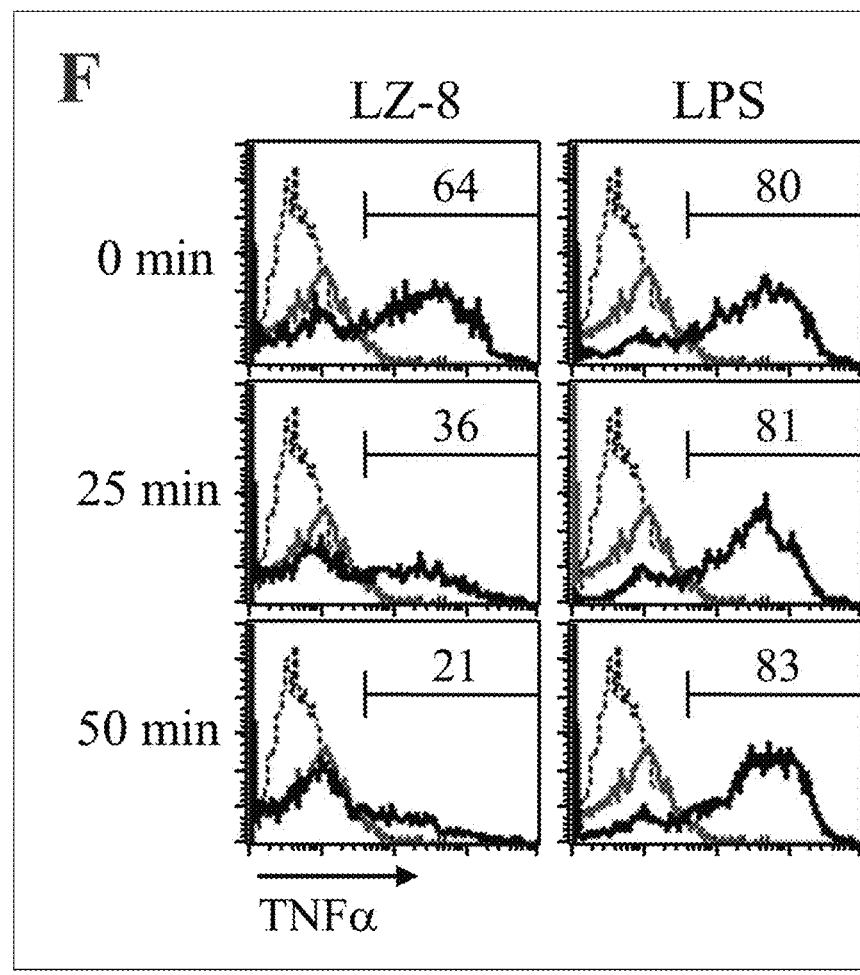
Figure 5A:
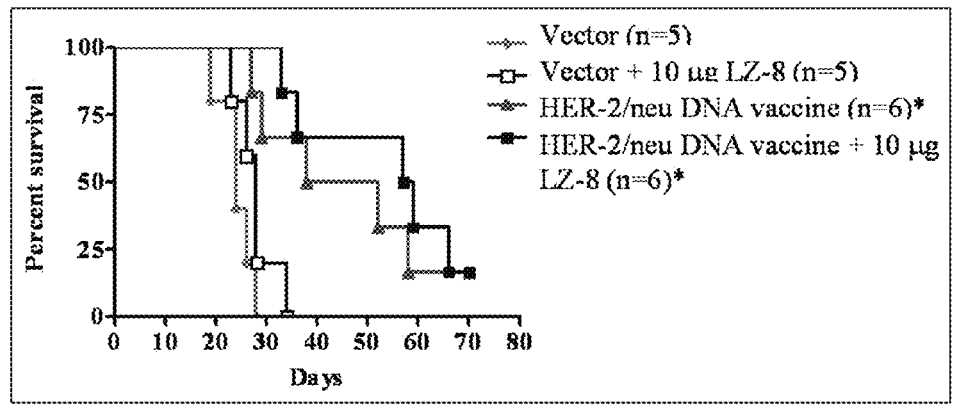
FIG. 5 shows that TLR4 plays a major role in the enhancing effect of LZ-8 on HER-2/neu DNA vaccine. The data are presented as the mean±SD of three mice. The experiments are repeated two times and similar results were obtained. The symbol (*) indicates a statistically significant difference when compared DNA vaccine-treated to control vector-treated mice ($p<0.001$). No significant difference between HER-2/neu DNA vaccine and HER-2/neu DNA vaccine plus 10 μg LZ-8 ($p=0.17$ in DC/T=50, $p=0.21$ in DC/T=25).
Figure 5B:
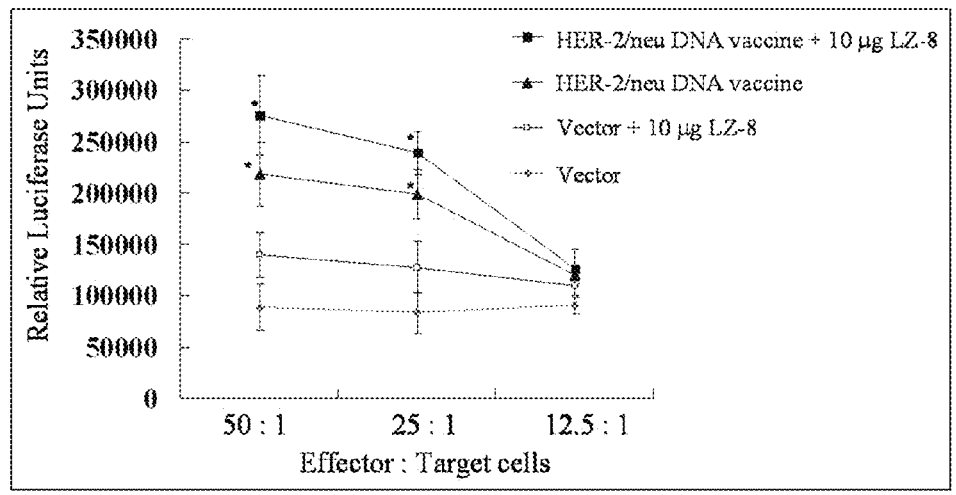

TLR4 has been shown to involve in LZ-8-induced DC activation (FIG. 1B). Thus, the present invention asked whether the enhanced efficacy of LZ-8-cotreated HER-2/neu DNA vaccine was related to TLR4. As shown in FIG. 5A, HER-2/neu DNA vaccine significantly prolonged the survival of tumor-bearing C3H/HeJ (TLR4 mutant) mice compared to control group; however, the co-treatment of LZ-8 (10 µg) had almost no effect on the efficacy of HER-2/neu DNA (p=0.69). Furthermore, limiting increment of the CTL activity was induced in TLR4 mutant mice immunized with HER-2/neu DNA vaccine plus LZ-8 when compared to the immunization of HER-2/neu DNA vaccine alone (p=0.17 in DC/T=50, p=0.21 in DC/T=25) (FIG. 5B). These results suggest that TLR4 is required for the adjuvanticity of LZ-8 on HER-2/neu DNA vaccine.

FIG. 5 shows that TLR4 played a major role in the enhancing effect of LZ-8 on HER-2/neu DNA vaccine. C3H/HeJ (TLR4 mutant) mice were implanted with MBT-2 tumor cells and then were inoculated with HER-2/neu DNA vaccines with various formulas as indicated. (A) Kaplan-Meier survival curves of surviving mice (%) as a function of time after tumor challenge. The symbol (*) indicates a statistically significant difference when compared DNA vaccine-treated to control vector-treated mice (p<0.05). There were no significant difference between HER-2/neu DNA vaccine and HER-2/neu DNA vaccine plus 10 µg LZ-8 (p=0.69). Similar data were obtained from two independent experiments. (B) As described in FIG. 4B, the activated LN cells from vaccinated C3H/HeJ mice were co-cultured with MBT-2-luciferase cells at indicated ratios and then luciferase activity in the supernatants was determined. The data are presented as the mean±SD of three mice. The experiments were repeated two times and similar results were obtained. The symbol (*) indicates a statistically significant difference when compared DNA vaccine-treated to control vector-treated mice (p<0.001). There were no significant difference between HER-2/neu DNA vaccine and HER-2/neu DNA vaccine plus 10 µg LZ-8 (p=0.17 in DC/T=50, p=0.21 in DC/T=25).

What is claimed is:

1. A method for augmenting immunogenicity of a naked DNA in a mammal, comprising immunizing the mammal with a composition comprising
   (i) the naked DNA, and
   (ii) an adjuvant in an effective amount to augment the immunogenicity of the naked DNA, wherein the adjuvant comprises a Ling-Zhi-8 (LZ-8) protein.

2. The method of claim 1, wherein the naked DNA is HER-2/neu DNA.

3. The method of claim 2, wherein the HER-2/neu DNA is delivered by gene gun.

4. The method of claim 1, wherein the LZ-8 protein is isolated from *Ganoderma lucidum* or prepared by recombinant protein technology in yeast or bacterium system.

5. The method of claim 1, wherein the antigen naked DNA and the adjuvant are administered simultaneously.

6. The method of claim 1, wherein the augmenting the immunogenicity is manifested by the enhancement of the T helper 1 (Th1) and cytotoxic T lymphocyte (CTL) response.

7. The method of claim 1, wherein the mammal is human.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: primer
<222> LOCATION: (1)..(20)

<400> SEQUENCE: 1
actggcaaaa ggatggtgac                                              20

<210> SEQ ID NO 2
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: primer
<222> LOCATION: (1)..(20)

<400> SEQUENCE: 2
acctgtgggt tgttgacctc                                              20

<210> SEQ ID NO 3
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(24)

<400> SEQUENCE: 3
gttggataag gccagacttt gttg                                         24
```

```
<210> SEQ ID NO 4
<211> LENGTH: 24
<212> TYPE: DNA
<213> ORGANISM: Artificial Sequence
<220> FEATURE:
<223> OTHER INFORMATION: primer
<220> FEATURE:
<221> NAME/KEY: primer_bind
<222> LOCATION: (1)..(24)

<400> SEQUENCE: 4
gattcaactt gcgccatctt aggc                                              24
```